(12) United States Patent
Hunt et al.

(10) Patent No.: US 7,553,306 B1
(45) Date of Patent: Jun. 30, 2009

(54) NEGATIVE PRESSURE THERAPY USING WALL SUCTION

(75) Inventors: Kenneth William Hunt, Dorset (GB); Keith Patrick Heaton, Dorset (GB)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 09/807,403

(22) PCT Filed: Oct. 13, 1999

(86) PCT No.: PCT/GB99/03392

§ 371 (c)(1), (2), (4) Date: Jul. 2, 2001

(87) PCT Pub. No.: WO00/21586

PCT Pub. Date: Apr. 20, 2000

(30) Foreign Application Priority Data

Oct. 13, 1998 (GB) ................................. 9822341.5

(51) Int. Cl.
A61F 13/00 (2006.01)
A61M 1/00 (2006.01)
A61M 27/00 (2006.01)

(52) U.S. Cl. .................. 604/543; 604/304; 604/305; 604/319

(58) Field of Classification Search ............... 604/35, 604/66, 67, 118–119, 289–290, 304–308, 604/313–315, 317–323, 327, 543; 602/42–43
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |

(Continued)

FOREIGN PATENT DOCUMENTS

AU 550575 A1 8/1982

(Continued)

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

(Continued)

*Primary Examiner*—Tatyana Zalukaeva
*Assistant Examiner*—Melanie J Hand

(57) ABSTRACT

Apparatus for applying negative pressure therapy to a wound site, which comprises an open celled foam pad for application to the wound, a suction tube connecting the foam pad to a collection canister having a shut-off valve which closes the outlet from the canister when it is full, a tube for connecting the canister to a wall suction point or to a vacuum bottle, and a pressure detecting device connected to the suction tube between the foam pad and the canister for indicating when the pressure in the suction tube falls below a predetermined level.

15 Claims, 3 Drawing Sheets

U.S. PATENT DOCUMENTS

| | | | |
|---|---|---|---|
| 3,520,300 A | | 7/1970 | Flower, Jr. |
| 3,568,675 A | | 3/1971 | Harvey |
| 3,648,692 A | | 3/1972 | Wheeler |
| 3,682,180 A | | 8/1972 | McFarlane |
| 3,826,254 A | | 7/1974 | Mellor |
| 4,051,431 A | * | 9/1977 | Wurster .................. 73/861 |
| 4,080,970 A | | 3/1978 | Miller |
| 4,096,853 A | | 6/1978 | Weigand |
| 4,139,004 A | | 2/1979 | Gonzalez, Jr. |
| 4,165,748 A | | 8/1979 | Johnson |
| 4,184,510 A | | 1/1980 | Murry et al. |
| 4,233,969 A | | 11/1980 | Lock et al. |
| 4,245,630 A | | 1/1981 | Lloyd et al. |
| 4,256,109 A | * | 3/1981 | Nichols ................ 604/320 |
| 4,261,363 A | | 4/1981 | Russo |
| 4,275,721 A | | 6/1981 | Olson |
| 4,284,079 A | | 8/1981 | Adair |
| 4,297,995 A | | 11/1981 | Golub |
| 4,333,468 A | | 6/1982 | Geist |
| 4,373,519 A | | 2/1983 | Errede et al. |
| 4,382,441 A | | 5/1983 | Svedman |
| 4,392,853 A | | 7/1983 | Muto |
| 4,392,858 A | | 7/1983 | George et al. |
| 4,419,097 A | | 12/1983 | Rowland |
| 4,465,485 A | | 8/1984 | Kashmer et al. |
| 4,475,909 A | | 10/1984 | Eisenberg |
| 4,480,638 A | | 11/1984 | Schmid |
| 4,525,166 A | | 6/1985 | Leclerc |
| 4,525,374 A | | 6/1985 | Vaillancourt |
| 4,540,412 A | | 9/1985 | Van Overloop |
| 4,543,100 A | | 9/1985 | Brodsky |
| 4,548,202 A | | 10/1985 | Duncan |
| 4,551,139 A | | 11/1985 | Plaas et al. |
| 4,569,348 A | | 2/1986 | Hasslinger |
| 4,605,399 A | | 8/1986 | Weston et al. |
| 4,608,041 A | | 8/1986 | Nielson |
| 4,640,688 A | | 2/1987 | Hauser |
| 4,655,754 A | | 4/1987 | Richmond et al. |
| 4,664,662 A | | 5/1987 | Webster |
| 4,710,165 A | | 12/1987 | McNeil et al. |
| 4,733,659 A | | 3/1988 | Edenbaum et al. |
| 4,743,232 A | | 5/1988 | Kruger |
| 4,758,220 A | | 7/1988 | Sundblom et al. |
| 4,787,888 A | | 11/1988 | Fox |
| 4,826,494 A | | 5/1989 | Richmond et al. |
| 4,838,883 A | | 6/1989 | Matsuura |
| 4,840,187 A | | 6/1989 | Brazier |
| 4,863,449 A | | 9/1989 | Therriault et al. |
| 4,872,450 A | | 10/1989 | Austad |
| 4,878,901 A | | 11/1989 | Sachse |
| 4,897,081 A | | 1/1990 | Poirier et al. |
| 4,906,233 A | | 3/1990 | Moriuchi et al. |
| 4,906,240 A | | 3/1990 | Reed et al. |
| 4,919,654 A | | 4/1990 | Kalt et al. |
| 4,941,882 A | | 7/1990 | Ward et al. |
| 4,953,565 A | | 9/1990 | Tachibana et al. |
| 4,969,880 A | | 11/1990 | Zamierowski |
| 4,985,019 A | | 1/1991 | Michelson |
| 5,037,397 A | | 8/1991 | Kalt et al. |
| 5,086,170 A | | 2/1992 | Luheshi et al. |
| 5,092,858 A | | 3/1992 | Benson et al. |
| 5,100,396 A | | 3/1992 | Zamierowski |
| 5,134,994 A | | 8/1992 | Say |
| 5,149,331 A | | 9/1992 | Ferdman et al. |
| 5,167,613 A | | 12/1992 | Karami et al. |
| 5,176,663 A | | 1/1993 | Svedman et al. |
| 5,215,522 A | | 6/1993 | Page et al. |
| 5,232,453 A | | 8/1993 | Plass et al. |
| 5,261,893 A | | 11/1993 | Zamierowski |
| 5,278,100 A | | 1/1994 | Doan et al. |
| 5,279,550 A | | 1/1994 | Habib et al. |
| 5,298,015 A | | 3/1994 | Komatsuzaki et al. |
| 5,342,376 A | | 8/1994 | Ruff |
| 5,344,415 A | | 9/1994 | DeBusk et al. |
| 5,354,268 A | * | 10/1994 | Peterson et al. ............... 604/35 |
| 5,358,494 A | | 10/1994 | Svedman |
| 5,437,622 A | | 8/1995 | Carion |
| 5,437,651 A | | 8/1995 | Todd et al. |
| 5,527,293 A | | 6/1996 | Zamierowski |
| 5,549,584 A | | 8/1996 | Gross |
| 5,556,375 A | | 9/1996 | Ewall |
| 5,607,388 A | | 3/1997 | Ewall |
| 5,636,643 A | | 6/1997 | Argenta et al. |
| 5,645,081 A | | 7/1997 | Argenta et al. |
| 5,669,892 A | | 9/1997 | Keogh et al. |
| 5,827,246 A | | 10/1998 | Bowen |
| 5,899,884 A | * | 5/1999 | Cover et al. ................. 604/119 |
| 5,944,703 A | * | 8/1999 | Dixon et al. ................ 604/319 |
| 6,071,267 A | | 6/2000 | Zamierowski |
| 6,135,116 A | | 10/2000 | Vogel et al. |
| 6,142,982 A | | 11/2000 | Hunt et al. |
| 6,241,747 B1 | | 6/2001 | Ruff |
| 6,287,316 B1 | | 9/2001 | Agarwal et al. |
| 6,345,623 B1 | | 2/2002 | Heaton et al. |
| 6,488,643 B1 | | 12/2002 | Tumey et al. |
| 6,493,568 B1 | | 12/2002 | Bell et al. |
| 6,553,998 B2 | | 4/2003 | Heaton et al. |
| 6,814,079 B2 | | 11/2004 | Heaton et al. |
| 2002/0077661 A1 | | 6/2002 | Saadat |
| 2002/0115951 A1 | | 8/2002 | Norstrem et al. |
| 2002/0120185 A1 | | 8/2002 | Johnson |
| 2002/0143286 A1 | | 10/2002 | Tumey |
| 2004/0064132 A1 | * | 4/2004 | Boehringer et al. ......... 604/543 |

FOREIGN PATENT DOCUMENTS

| | | | |
|---|---|---|---|
| AU | | 745271 | 4/1999 |
| AU | | 755496 | 2/2002 |
| CA | | 2005436 | 6/1990 |
| DE | | 26 40 413 A1 | 3/1978 |
| DE | | 43 06 478 A1 | 9/1994 |
| DE | | 295 04 378 U1 | 10/1995 |
| DE | | 197 22 075 | 10/1998 |
| DE | | 197 22 075 C1 | 10/1998 |
| EP | | 0100148 A1 | 2/1984 |
| EP | | 0117632 A2 | 9/1984 |
| EP | | 0161865 A2 | 11/1985 |
| EP | | 0 358 302 | 3/1990 |
| EP | | 0 853 950 | * 8/1995 |
| EP | | 1018967 B1 | 8/2004 |
| GB | | 692578 | 6/1953 |
| GB | | 2 195 255 A | 4/1988 |
| GB | | 2 220 357 A | 1/1990 |
| GB | | 2 235 877 | 3/1991 |
| GB | | 2307180 A | * 5/1997 |
| GB | | 2 197 789 A | 6/1998 |
| GB | | 2 329 127 | 3/1999 |
| GB | | 2 333 965 | 8/1999 |
| JP | | 4129536 | 4/1992 |
| JP | | 05-208046 | 8/1993 |
| JP | | 7-503520 | 4/1995 |
| JP | | 9-507138 | 7/1997 |
| JP | | 10-504484 | 5/1998 |
| SG | | 71559 | 4/2002 |
| WO | | WO 80/02182 | 10/1980 |
| WO | | WO 87/04626 | 8/1987 |
| WO | | WO 90/10424 | 9/1990 |
| WO | | WO 93/09727 | 5/1993 |
| WO | | WO 94/20041 | 9/1994 |
| WO | | 96/05873 | 2/1996 |
| WO | | 9605873 A1 | * 2/1996 |
| WO | | 97/18007 | 5/1997 |

WO 99/13793 3/1999

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986); pp. 94-96 (certified translation).

Chariker, Mark E., M.D., et al; "Effective Management of incisional and cutaneous fistulae with closed suction wound drainage"; Contemporary Surgery, vol. 34, Jun. 1989, pp. 59-63.

Engell Minor, Instruction Book, First Edition, 300 7502, Feb. 1975, pp. 24.

Engell Minor: Addition to the Users Manual Concerning Overflow Protection - Concerns all Engell Pumps, Feb. 3, 1983, p. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: " A Dressing Allowing Continuous treatment of a Biosurface", IRCS Medical Science: Biomedical technology, Clinical Medicine, Surgery and Transplantation, vol. 7, 1979, p. 221.

Svedman, P. et al.: "A Dressing System Providing Fluid Supply and Suction Drainage Used for Continuous of Intermitten Irrigation", Annals of Plastic Surgery, vol. 17, No. 2, Aug. 1986, pp. 125-133.

K.F. Jeter, T.E. Tintle, and M. Chariker, Managing Draining Wounds and Fistulae: "New and Established Methods," *Chronic Wound Care*, edited by D. Krasner (Health Mangement Publications, Inc., King of Prussia, PA 1990), pp. 240-246.

G. Živadinović, V. Ðukić, Ž. Maksimović, Ð. Radak, and O. Peška, "Vacuum Therapy in the Treatment of Peripheral Blood Vessels," *Timok Medical Journal* 11 (1986), pp. 161-164 (copy and certified translation).

F.E. Johnson, "An Improved Technique for Skin Graft Placement Using a Suction Drain," *Surgery, Gynecology, and Abstetrics* 159 (1984), pp. 584-585.

A.A. Safronov, Dissertation Abstract, *vacuum Therapy of Trophic Ulcers of the Lower Leg with Simultaneous Autoplasty of the Skin* (Central Scientifc Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax, " *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

\* cited by examiner

NEGATIVE PRESSURE THERAPY USING WALL SUCTION

This invention relates to negative pressure therapy and provides a device which can be used to provide such therapy on connection to an existing source of suction, such as a vacuum fine.

Our prior patent application WO 97/18007 describes portable wound treatment apparatus for stimulating the healing of wounds. The apparatus described in our above application comprises a porous pad, which is permeable to fluids, for packing into or over the wound, dressings for covering and for providing an air-tight seal around the wound, and a drainage tube connecting the pad to a suction pump so that negative pressure can be applied to the wound to draw fluids therefrom, a canister being provided for collecting fluids which are sucked from the wound.

The apparatus described in our above application can be worn by the patient on a harness or sling so that he is not confined to one particular place while the therapy is in progress. There is, however, a demand for a more basic piece of equipment which, although not as sophisticated as the equipment described in our above application, does provide some of the benefits of negative pressure therapy.

Most hospitals have a suction line which is fed to all the wards and is available to nursing staff for a variety of purposes, such as powering drainage tubes and suctioning body fluids generally. For such uses, a pressure regulator may be connected to the source of suction and this regulator may include a pressure gauge indicating the pressure at the regulator valve. It is, however, dangerous to connect such a suction source directly with a patient, without providing continuous supervision. In many hospitals, shortage of staff makes it difficult or impossible to provide adequate close supervision, and if attempts are made to use such a source for negative pressure therapy, there is a very real danger of injuring the patient.

In some hospitals, vacuum bottles may be employed to assist drainage from wounds, e.g. after operations. Such bottles are containers which are available in various capacities and which are evacuated to low pressure. Vacuum bottles can be used in accordance with the invention as an alternative to a wall suction point. They have the advantage of providing a greater degree of portability to the negative pressure therapy apparatus, but the disadvantage that the bottle needs to be replaced with a fresh bottle once the pressure in the bottle has increased to the vicinity of ambient pressure.

An object of the present invention is to provide equipment which can be used with an existing wall suction source to safely provide negative therapy to patients.

According to one aspect of the present invention there is provided apparatus for applying negative pressure therapy to a wound site, said apparatus comprising an open celled foam pad for application to the wound, a suction tube connecting the foam pad to a collection canister, said canister having a shut-off valve which closes the outlet from the canister when it is full, a tube for connecting the canister to a wall suction point or a vacuum bottle and a pressure detecting means connected to the suction tube between the foam pad and the canister for indicating when the pressure in the suction tube falls below a predetermined level. The pressure detecting means may be a transducer which is connected by a branch tube to the suction tube leading from the foam pad to the canister. The transducer may be set to generate a visible and/or audible warning when the pressure in the suction tube falls below a pre-set level. A sudden pressure drop in the suction line would indicate that the canister is full and, consequently, there is no longer any effective therapy being applied to the therapy.

The canister full situation would normally be indicated by substantially zero pressure in the suction line. The transducer may also be set to activate a warning in the event that the pressure in the suction line does not reach a minimum pre-set pressure, or the pressure rises towards atmospheric after suction has initially been established, thereby indicating a gross leak in the system.

Preferably, the apparatus also includes a flow limiter in the line connecting the canister to the wall suction source so as to prevent the flow in the suction tube exceeding a pre-set level.

The apparatus may include a display panel which indicate the pressure existing at any one moment in the suction line. The transducer may also be adjustable so that indication or warning is given at different pre-set pressures.

The apparatus as described above may be adapted to give intermittent pressure therapy by providing a relief valve in a tube leading from the suction line. This relief valve may be programmable by a processor so that it is openable and closeable according to a pre-set programme thereby providing intermittent negative pressure therapy to the wound site.

Further features described below may also be introduced into the apparatus as described to give further desirable features.

Several embodiments in accordance with the invention will now be described with reference to the accompanying drawings, in which.

Figure 1:
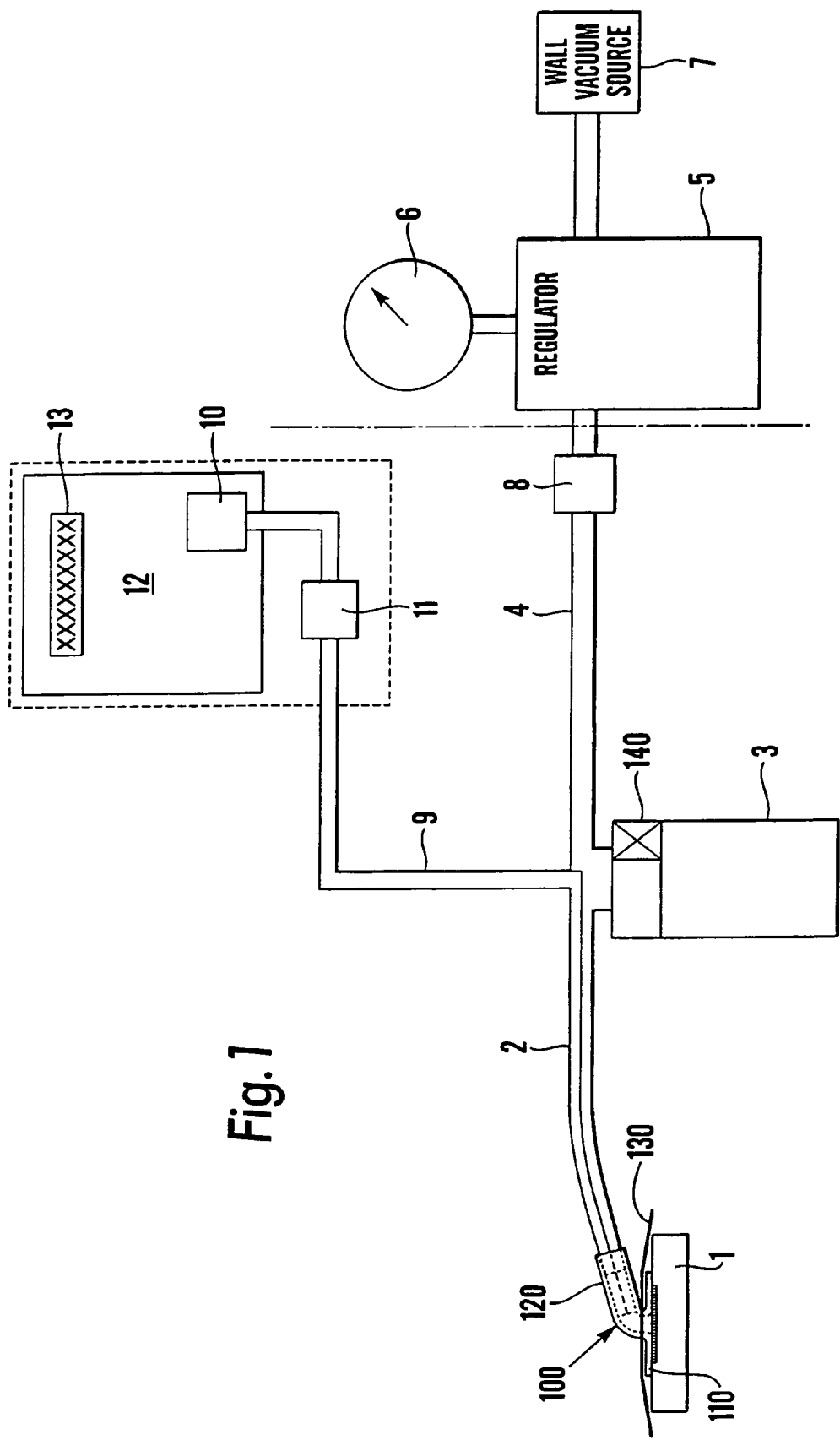
FIG. 1 is a diagrammatic representation of one embodiment in accordance with the invention.

Referring to FIG. 1 of the drawings, the apparatus for applying negative therapy comprises a foam pad (1) which is applied over or packed into a wound to be treated and is connected by a suction tube (2) to a canister (3). The canister (3) may be of conventional design having a shut-off valve (shown diagrammatically at (140), which automatically closes once the canister is full. The foam pad may comprise any suitable interconnected cellular foam. Foams which have been found to be especially suitable are polyurethane and polyvinyl alcohol foams or combinations thereof, having interconnected cells.

Figure 2:
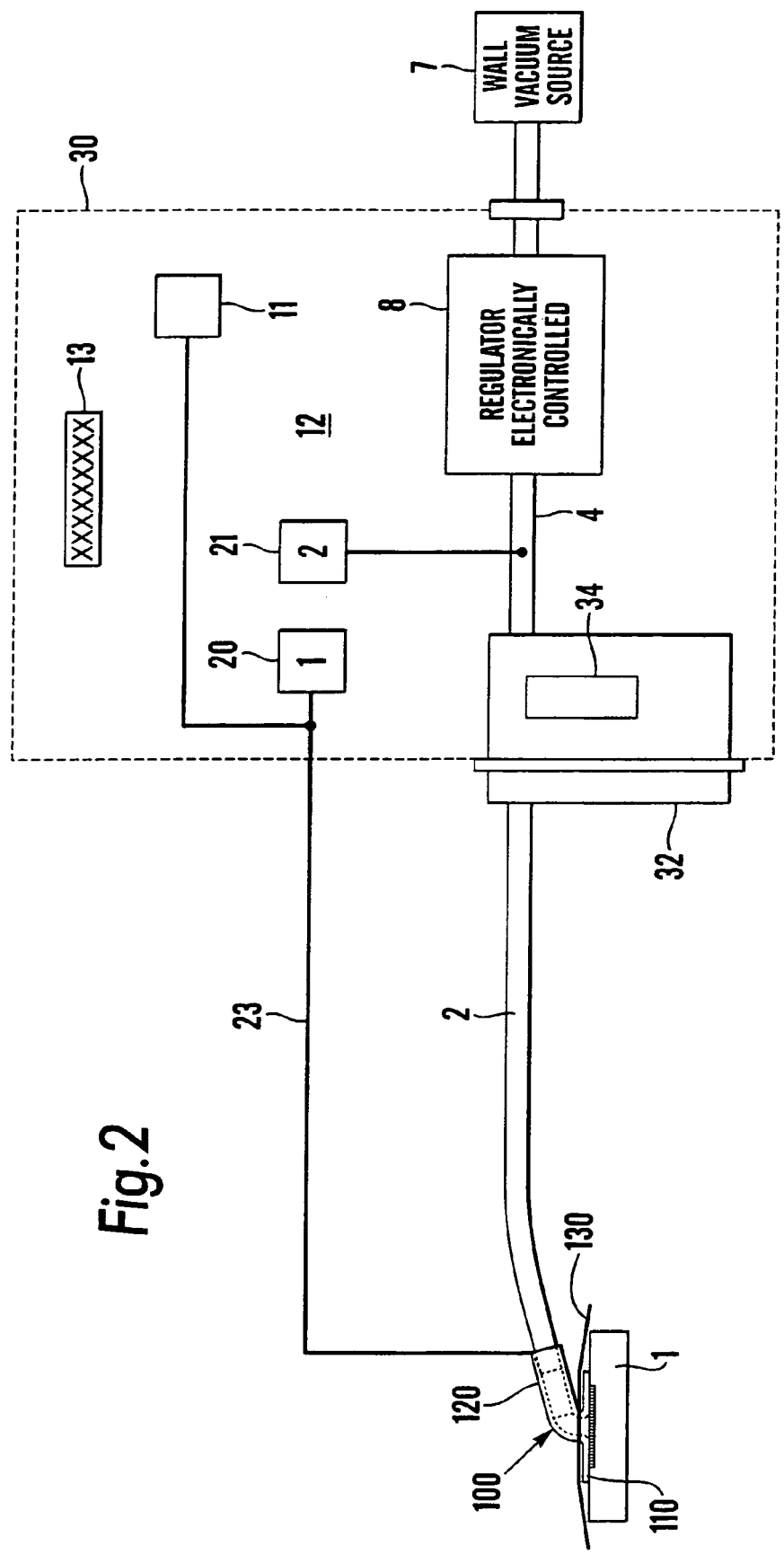
FIG. 2 is a diagrammatic representation of a second embodiment.

As shown in FIGS. 1 and 2, the foam pad is packed into the open wound and connected to the negative pressure source by a connector device (100) comprising a flexible backing plate (110) and an integral connector tube (120). The connector tube (120) is dimensioned internally to receive the suction tube or tubes (2) as a substantially air-tight fit. The foam pad and connector combination is secured to the wound to be treated by a surgical drape (130), which may be formed with an aperture to permit the tubular part (120) of the connector to pass through the drape.

A connector of this kind is described in UK Patent Application No. 9819678.5, WO 99/13793 and the corresponding U.S. patent application Ser. No. 09/350,581 filed on 9 Jul. 1999 entitled "Surgical drape and suction head for wound treatment", the disclosure of which is specifically incorporated herein.

A suitable canister of this kind is described in WO 97/18007, European Patent Application No. 0358302 or in U.S. patent application Ser. No. 09/078,223, the disclosure of which is specifically incorporated herein. The canister is also connected via a further tube (4) to a pressure regulator (5). The pressure regulator carries a gauge (6) and is connected to an existing vacuum line such as a standard hospital wall suction source (7). In many hospital installations a regulator valve (5), together with a pressure gauge (6) already exist, attached to an existing suction source or can be fitted to an existing outlet in the suction source supply. The apparatus may also include an optional flow limiter (8), which may be adjusted to provide different desired levels of flow in the system.

Pressure in the suction tube (2) is measured by a branch tube (9) which is connected to the suction tube and to a transducer (10). The transducer (10) is mounted on a process control board (12) and this may be connected to a visual display (13). An optional relief valve (11) may also be connected into the tube (9) and provide a means for controlling the level of negative pressure at the wound site. The relief valve (11) may be manually settable so that the pressure at the wound site does not exceed a predetermined figure. In a more esoteric version, the relief valve may be electronically controlled from the PCB to relieve pressure at the wound site at pre-settable maximum pressures. Many hospitals, in addition to having a suction source and a pressure regulator such as regulator (5), also have body fluid collection canisters (3) supplied for other purposes. It may, therefore, be possible to supply to the hospital apparatus included in the dotted line shown in FIG. 1, together with foams and connecting tubes so that they can connect the existing apparatus to a canister and a regulator (5) available in the hospital.

A more elaborate system is shown in FIG. 2, which is similar to the arrangement shown in FIG. 1 except for the following features described below. The same reference numerals indicate features common to both embodiments. First, the pressure regulator 15 connecting the apparatus to the wall suction source 17 is electronically controlled by the process control board (12). Secondly, the pressure at the wound site is monitored by a transducer (20), while the pressure in the tube connecting the canister to the regulator is measured by a transducer (21). The transducer (20) is connected to the wound side by a tube (23). Instead of providing separate tubes (2) and (23), a single bi- or multi-lumen tube rnay be used as described in our co-pending application WO97/18007. A relief valve (24) communicates with the tube (23) and enables the apparatus to operate intermittently in a controllable manner by intermittently reducing flow through the regulator (8) and venting pressure through the valve (11). The canister full situation is detected by noting a pressure differential between transducer (20) and transducer (21), or by means of a separate fluid level sensor. Pressure detection at the wound site via the transducer (20) also indicates whether there is a pressure leak or no therapy. A custom-made canister (32) may include means for sensing electronically when the canister is full and must be replaced, e.g. by capacitance measuring means (34). Preferably, the canister is designed to fit into a recess in a custom made housing (30), indicated by dotted lines. The housing may be directly connected at one end to the wall suction point (7), and at the other to a tube or tubes leading to the foam pad (1) at the wound site.

In the embodiment of FIG. 2, the transducers (20 & 21), the relief valve (11) and pressure regulator (8) are preferably all electronically controlled by connections to the PCB. For example, the canister full situation is detected by comparison of the pressure difference between transducers (20 & 21) and this can be signalled on the display (13) and, optionally, also by an audible warning signal.

Figure 3A:
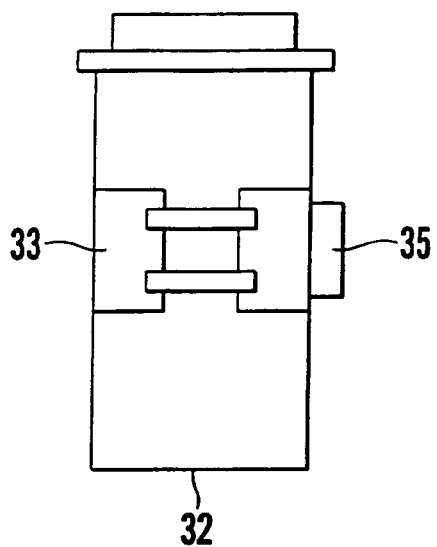
FIGS. 3A & 3B are diagrammatic representations of a collection canister for monitoring rates of flow of fluids sucked from the wound.

It may be desirable to measure the rate at which fluids are sucked from the wound site. This is conveniently achieved by measuring the rate at which the canister is filled with wound exudate. A suitable device is shown diagrammatically in FIG. 3. In one configuration shown in FIG. 3A, a sleeve (33) is held in intimate contact with the outer surface of the canister. This sleeve carries a single sensing element (35), e.g. capacitive sensor that can provide a means of sensing the presence of liquid at different levels in the canister by simply moving the sleeve up and down the canister. The sensing element detects the presence of liquid by projecting an electrical field into the canister and detecting any change in that field, e.g. by a change in capacitance. The rate of change of capacity over the portion of the canister surveyed by the detector gives an indication of rate of flow of fluid sucked from the wound site.

Figure 3B:
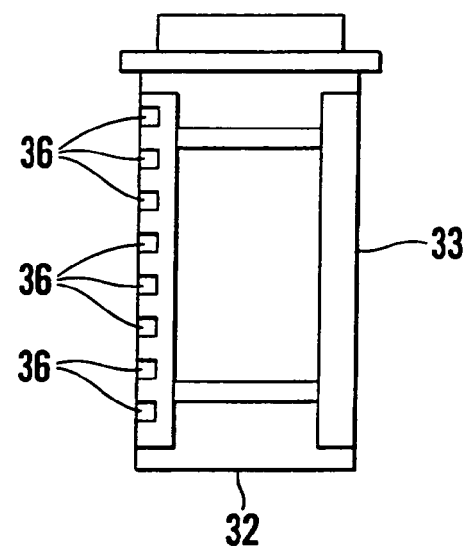

In another configuration shown in FIG. 3B, a series of sensing elements (36) are evenly spaced on a sleeve (33) that is in contact with the outer surface of the canister. As the fluid level rises within the canister, the sensing elements are triggered. This information can then be used by the control system at the PCB to deduce flow rate.

The invention claimed is:

1. Apparatus for applying negative pressure therapy to a wound site, which comprises an open celled foam pad for application to the wound site, a suction tube connecting the foam pad to a collection canister, said canister having a shut-off valve which closes an outlet from the canister in response to the collection canister being full, a tube connecting the canister to a wall suction point, and a pressure detector connected to the suction tube between the foam pad and the canister for indicating when the pressure in the suction tube crosses a predetermined level.

2. Apparatus as claimed in claim 1, further comprising a flow limiting valve disposed between the canister and the wall suction point, the flow limiting valve allowing adjustment of the flow to a selected rate such that flow in the tube does not exceed the selected rate.

3. Apparatus as claimed in claim 1 which includes a pressure relief valve which is connected to the suction tube between the foam pad and the canister.

4. Apparatus as claimed in claim 1, further comprising a first transducer for measuring pressure in the tube linking the canister to the wall suction point, and wherein the pressure detector connected to the suction tube between the foam pad and the canister comprises a second transducer.

5. Apparatus as claimed in claim 1 which includes a flow rate meter for measuring the rate at which fluid is drawn from the wound site.

6. Apparatus as claimed in claim 5 in which the flow rate meter measures the rate at which the canister is filled.

7. Apparatus as claimed in claim 6 in which the flow rate meter is an electrical capacitance measuring device.

8. Apparatus for applying negative pressure therapy to a wound site, which comprises an open-celled foam pad for application to the wound site, a suction tube connecting the foam pad to a collection canister, a tube connecting an outlet of the canister to a wall suction point, a sensor operable to detect when the canister is full, and a shut-off valve fluidly connected to the outlet of the canister to close the outlet in response to the collection canister being full.

9. Apparatus according to claim 8 which includes means for giving a warning that the canister is full and/or shutting off a connection between the canister and the wall suction point.

10. Apparatus according to claim 8 which further includes means for monitoring pressure at the wound site.

11. Apparatus according to claim 8 which further includes means for regulating pressure between the canister and the wall suction point.

12. Apparatus as claimed in claim 1 in which the pressure detector comprises a transducer connected by a branch tube to the suction tube leading from the foam pad to the canister.

13. Apparatus as claimed in claim 3, further comprising a processor operationally coupled to the relief valve and programmed to provide intermittent negative pressure therapy to the wound site.

14. Apparatus for applying negative pressure therapy to a wound site, the apparatus comprising:
- an open-celled foam pad for application to the wound site;
- a suction tube connecting the foam pad to a collection canister;
- a pressure regulator fluidly connected between the canister and a wall suction point; and
- a processor in electronic communication with the pressure regulator to regulate the pressure from said wall suction point to the collection canister.

15. The apparatus of claim 14, wherein the pressure regulator includes a relief valve, and wherein the processor is configured to actuate the relief valve to relieve pressure at the wound site when pressure at the wound site reaches a set maximum pressure.

\* \* \* \* \*